US007402303B2

(12) United States Patent
Proudfoot et al.

(10) Patent No.: US 7,402,303 B2
(45) Date of Patent: Jul. 22, 2008

(54) CHEMOKINE MUTANTS IN THE TREATMENT OF MULTIPLE SCLEROSIS

(75) Inventors: Amanda Proudfoot, Chens-sur-Léman (FR); Timothy N. C. Wells, Prevessin Moens (FR); Marie Kosco-Vilbois, Minzier (FR)

(73) Assignee: Laboratoires Serono SA, Coinsins, Vaud (CH)

( * ) Notice: Subject to any disclaimer, the term of this patent is extended or adjusted under 35 U.S.C. 154(b) by 148 days.

(21) Appl. No.: 10/398,457

(22) PCT Filed: Oct. 3, 2001

(86) PCT No.: PCT/EP01/11428

§ 371 (c)(1),
(2), (4) Date: Nov. 13, 2003

(87) PCT Pub. No.: WO02/28419

PCT Pub. Date: Apr. 11, 2002

(65) Prior Publication Data

US 2004/0101509 A1    May 27, 2004

(30) Foreign Application Priority Data

Oct. 4, 2000    (EP) .................................. 00121665

(51) Int. Cl.
*A61K 45/00* (2006.01)
*C12P 21/00* (2006.01)
(52) U.S. Cl. ..................................... 424/85.1; 435/69.5
(58) Field of Classification Search ....................... None
See application file for complete search history.

(56) References Cited

U.S. PATENT DOCUMENTS 5,854,412 A    12/1998    Rollins et al.

FOREIGN PATENT DOCUMENTS

| WO | WO 98 06751 | | 2/1998 |
| WO | WO 99 33989 | | 7/1999 |
| WO | WO 99/33989 | * | 7/1999 |
| WO | WO 9933989 A2 | * | 7/1999 |
| WO | WO 00 44408 | | 8/2000 |

OTHER PUBLICATIONS

Fritchley et al., Immunology, Dec. 1999 98(Suppl. 1):47 (Abstract).*
Proudfoot et al., J. Biol. Chem., vol. 276, p. 10620-10626, published online on Dec. 14, 2000.*
Hvas et al., Scand J Immunol. Aug. 1997;46(2):195-203.*
Trebst et al., Curr Phar Des. 2006;12(2):241-9, Abstract.*
Chaudri, Lancet Feb. 11, 2006, 367:472-473.*
Schall et al., J Immunol Aug. 1, 1988;141(3):1018-25.*
UniProt Basic UniProtKB Entry Viewer Protein CCL5_Human (Jul. 15, 1999).*
Appay, Victor, et al. "Aggregation of RANTES is Responsible for Its Inflammatory Properties", *The Journal of Biological Chemistry*, vol. 274, No. 39, Sep. 24, 1999, p. 27505-27512.
Czaplewski, Lloyd, et al. "Identification of Amino Acid Residues Critical for Aggregation of Human CC Chemokines Macrophage Inflammatory Protein (MIP)-1α, MIP-1β, and RANTES", *The Journal of Biological Chemistry*, vol. 274, No. 23, Jun. 4, 1999, p. 16077-16084.
Fritchley, Sara J., et al. "Identification Of Heparan Sulphate Binding Site In Rantes: Consequences For Leukocyte Activation", *Immunology*, vol. 98, No. suppl.1, Dec. 1999, p. 47,(Joint Congress of the British Society for Immunology and the British Society for Allergy & Clinical Immunology, Harrogate, England, UK); XP-001010396.
Graham, Gerard, et al., "Uncoupling of stem cell inhibition from monocyte chemoattraction in the MIP-1α by mutagenesis of the proteoglycan binding site", *The EMBO Journal*, vol. 15, No. 23, 1996, p. 6506-6515, (Oxford University Press); XP-002173221.
Hoogewerf, Arlene, et al., "Glycosaminoglycans Mediate Cell Surface Oligomerization of Chemokines", *Biochemistry*, vol. 36, 1997, p. 13570-13578.
Koopmann, Witte, et al. "Identification of a Glycosaminoglycan-binding Site in Chemokine Macrophage Inflammatory Protein-1α", *The Journal of Biological Chemistry*, vol. 272, No. 15, Apr. 11, 1997, p. 10103-10109; XP-002171678.
Kuschert, Gabriele, et al. "Glycosaminoglycans Interact Selectively with Chemokines and Modulate Receptor Binding and Cellular Responses", *Biochemistry*, vol. 38, 1999, p. 12959-12968.
Laurence, Jennifer, et al al. "Importance of Basic Residues and Quaternary Structure in the Function on MIP-1β: CCR5 Binding and Cell Surface Sugar Interactions", *Biochemistry*, vol. 40, No. 16, Apr. 24, 2001, p. 4990-4999; XP-002193384.
Proudfoot, Amanda, "Probing the role of the GAC/Chemokine interaction", Chemokine Gordon Conference (Session 1, Jul. 24, 2000).
Proudfoot, Amanda, et al., "The BBXB Motif of RANTES Is the Principal Site of Heparin Binding and Controls Receptor Selectivity", *The Journal of Biological Chemistry*, vol. 276, No. 14, Apr. 6, 2001, p. 10620-10626.
Schwartz, Matthew and Wells, Timothy NC, "Intefering with chemokine networks—the hope for new therapeutics", *Current Opinion in Chemical Biology*, vol. 3, 1999, p. 407-417.

* cited by examiner

*Primary Examiner*—Gary B. Nickol
*Assistant Examiner*—Cherie Woodward
(74) *Attorney, Agent, or Firm*—Browdy and Neimark, PLLC

(57) ABSTRACT

Mutants of CC chemokines, which contain at least two mutations in the cationic site of the 40's loop and which, relative to the wild-type molecule, have a reduced GAG-binding activity. In particular it has been found that such mutated chemokines are effective in the treatment of multiple sclerosis and/or demyelinating diseases. A triple mutant of RANTES is the compound showing the best results.

2 Claims, 11 Drawing Sheets

WT (O); Triple 50's mutant (▲); Triple 40's mutant (●)

WT (O); Triple 50's mutant (▲); Triple 40's mutant (●)

WT (○); Triple 50's mutant (▲); Triple 40's mutant (●)

Figure 10 cells x 10$^6$

15 —

10 —

5 —

0 —

Baseline    NaCl    triple 40's
                    RANTES mutant
                    (10 µg)

SEQUENCE LISTING

<160> NUMBER OF SEQ ID NOS: 40

<210> SEQ ID NO 1
<211> LENGTH: 91
<212> TYPE: PRT
<213> ORGANISM: Homo sapiens
<220> FEATURE:
<221> NAME/KEY: SIGNAL
<222> LOCATION: (1)..(23)

<400> SEQUENCE: 1

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 2
<211> LENGTH: 66
<212> TYPE: PRT
<213> ORGANISM: Pichia Pastoris

<400> SEQUENCE: 2

Tyr Ser Ser Asp Thr Thr Pro Cys Cys Phe Ala Tyr Ile Ala Arg Pro
1               5                   10                  15

Leu Pro Arg Ala His Ile Lys Glu Tyr Phe Tyr Thr Ser Gly Lys Cys
                20                  25                  30

Ser Asn Pro Ala Val Val Phe Val Thr Ala Ala Asn Ala Gln Val Cys
            35                  40                  45

Ala Asn Pro Glu Lys Lys Trp Val Arg Glu Tyr Ile Asn Ser Leu Glu
        50                  55                  60

Met Ser
65

<210> SEQ ID NO 3
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 3

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Ala Ala Asn Ala Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 4
<211> LENGTH: 70
<212> TYPE: PRT
<213> ORGANISM: Escherichia Coli

<400> SEQUENCE: 4

Ala Ser Leu Ala Ala Asp Thr Pro Thr Ala Cys Cys Phe Ser Tyr Thr
1               5                   10                  15

Ser Ala Gln Ile Pro Gln Asn Phe Ile Ala Asp Tyr Phe Glu Thr Ser
                20                  25                  30

Ser Gln Cys Ser Lys Pro Gly Val Ile Phe Leu Thr Lys Ala Ser Ala
            35                  40                  45

Gln Val Cys Ala Asp Pro Ser Glu Glu Trp Val Gln Lys Tyr Val Ser
        50                  55                  60

Asp Leu Glu Leu Ser Ala
65                  70

<210> SEQ ID NO 5
<211> LENGTH: 69
<212> TYPE: PRT
<213> ORGANISM: Escherichia Coli

<400> SEQUENCE: 5

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
                20                  25                  30

Ser Leu Cys Ser Gln Pro Ala Val Val Phe Gln Thr Ala Ala Ser Ala
            35                  40                  45

Gln Val Cys Ala Asp Pro Ser Glu Ser Trp Val Gln Glu Tyr Val Tyr
        50                  55                  60

Asp Leu Glu Leu Asn
65

<210> SEQ ID NO 6
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 6

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Ala Ala Trp
65                  70                  75                  80

Val Ala Glu Tyr Ile Asn Ser Leu Glu Met Ser
                85                  90

-continued

```
<210> SEQ ID NO 7
<211> LENGTH: 92
<212> TYPE: PRT
<213> ORGANISM: Escherichia Coli

<400> SEQUENCE: 7
```

Met Lys Val Ser Ala Ala Ala Leu Ala Val Ile Leu Ile Ala Thr Ala
1               5                   10                  15

Leu Cys Ala Pro Ala Ser Ala Met Ser Pro Tyr Ser Ser Asp Thr Thr
                20                  25                  30

Pro Cys Cys Phe Ala Tyr Ile Ala Arg Pro Leu Pro Arg Ala His Ile
            35                  40                  45

Lys Glu Tyr Phe Tyr Thr Ser Gly Lys Cys Ser Asn Pro Ala Val Val
    50                  55                  60

Phe Val Thr Ala Ala Asn Ala Gln Val Cys Ala Asn Pro Glu Lys Lys
65                  70                  75                  80

Trp Val Arg Glu Tyr Ile Asn Ser Leu Glu Met Ser
                85                  90

```
<210> SEQ ID NO 8
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 8
```

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
    50                  55                  60

Val Thr Ala Lys Asn Arg Gln Val Cys Ala Asn Pro Glu Lys Lys Trp
65                  70                  75                  80

Val Arg Glu Tyr Ile Asn Ser Leu Glu Met Ser
                85                  90

```
<210> SEQ ID NO 9
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 9
```

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
    50                  55                  60

Val Thr Arg Ala Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 10
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 10

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Ala Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 11
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 11

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Ala Lys Trp
65                  70                  75                  80

Val Arg Glu Tyr Ile Asn Ser Leu Glu Met Ser
                85                  90

<210> SEQ ID NO 12
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 12

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Ala Trp
65                  70                  75                  80

Val Arg Glu Tyr Ile Asn Ser Leu Glu Met Ser
                85                  90

<210> SEQ ID NO 13
<211> LENGTH: 91
<212> TYPE: PRT
<213> ORGANISM: Escherichia coli
<220> FEATURE:
<221> NAME/KEY: SIGNAL
<222> LOCATION: (1)..(23)

<400> SEQUENCE: 13

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Lys Trp
65                  70                  75                  80

Val Ala Glu Tyr Ile Asn Ser Leu Glu Met Ser
                85                  90

<210> SEQ ID NO 14
<211> LENGTH: 25
<212> TYPE: DNA
<213> ORGANISM: Escherichia coli

<400> SEQUENCE: 14
tttgtcaccg caaagaaccg ccaag                                               25

<210> SEQ ID NO 15
<211> LENGTH: 25
<212> TYPE: DNA
<213> ORGANISM: Escherichia coli

<400> SEQUENCE: 15
gacgactgct gggttggagc acttg                                               25

<210> SEQ ID NO 16
<211> LENGTH: 25
<212> TYPE: DNA
<213> ORGANISM: Escherichia coli

<400> SEQUENCE: 16
tttgtcaccc gagcgaaccg ccaag                                               25

<210> SEQ ID NO 17
<211> LENGTH: 25
<212> TYPE: DNA
<213> ORGANISM: Escherichia coli

```
<400> SEQUENCE: 17
gacgactgct gggttggagc acttg                                           25

<210> SEQ ID NO 18
<211> LENGTH: 25
<212> TYPE: DNA
<213> ORGANISM: Escherichia coli

<400> SEQUENCE: 18
cgaaagaacg cccaagtgtg tgcca                                           25

<210> SEQ ID NO 19
<211> LENGTH: 25
<212> TYPE: DNA
<213> ORGANISM: Escherichia coli

<400> SEQUENCE: 19
ggtgacaaag acgactgctg ggttg                                           25

<210> SEQ ID NO 20
<211> LENGTH: 36
<212> TYPE: DNA
<213> ORGANISM: Escherichia coli

<400> SEQUENCE: 20
tttgtcaccg cagcgaacgc ccaagtgtgt gccaac                               36

<210> SEQ ID NO 21
<211> LENGTH: 27
<212> TYPE: DNA
<213> ORGANISM: Escherichia coli

<400> SEQUENCE: 21
gacgactgct gggttggagc acttgcc                                         27

<210> SEQ ID NO 22
<211> LENGTH: 27
<212> TYPE: DNA
<213> ORGANISM: Escherichia coli

<400> SEQUENCE: 22
gccaacccag aggcgaaatg ggttcgg                                         27

<210> SEQ ID NO 23
<211> LENGTH: 27
<212> TYPE: DNA
<213> ORGANISM: Escherichia coli

<400> SEQUENCE: 23
acacacttgg cggttctttc gggtgac                                         27

<210> SEQ ID NO 24
<211> LENGTH: 27
<212> TYPE: DNA
<213> ORGANISM: Escherichia coli

<400> SEQUENCE: 24
aacccagaga aggcatgggt tcgggag                                         27

<210> SEQ ID NO 25
<211> LENGTH: 27
<212> TYPE: DNA
```

<210> SEQ ID NO 25
<211> LENGTH: 27
<212> TYPE: DNA
<213> ORGANISM: Escherichia coli

<400> SEQUENCE: 25
ggcacacact tggcggttct ttcgggt                                27

<210> SEQ ID NO 26
<211> LENGTH: 27
<212> TYPE: DNA
<213> ORGANISM: Escherichia coli

<400> SEQUENCE: 26
aagaaatggg ttgcggagta catcaac                                27

<210> SEQ ID NO 27
<211> LENGTH: 24
<212> TYPE: DNA
<213> ORGANISM: Escherichia coli

<400> SEQUENCE: 27
ctctgggttg gcacacactt ggcg                                   24

<210> SEQ ID NO 28
<211> LENGTH: 36
<212> TYPE: DNA
<213> ORGANISM: Escherichia coli

<400> SEQUENCE: 28
gccaacccag aggcggcatg ggttgcggag tacatc                      36

<210> SEQ ID NO 29
<211> LENGTH: 33
<212> TYPE: DNA
<213> ORGANISM: Escherichia coli

<400> SEQUENCE: 29
acacacttgg cggttctttc gggtgacaaa gac                         33

<210> SEQ ID NO 30
<211> LENGTH: 74
<212> TYPE: PRT
<213> ORGANISM: Escherichia coli

<400> SEQUENCE: 30

Ser Lys Ser Met Gln Val Pro Phe Ser Arg Cys Cys Phe Ser Phe Ala
1               5                   10                  15

Glu Gln Glu Ile Pro Leu Arg Ala Ile Leu Cys Tyr Arg Asn Thr Ser
            20                  25                  30

Ser Ile Cys Ser Asn Glu Gly Leu Ile Phe Lys Leu Lys Arg Gly Lys
        35                  40                  45

Glu Ala Cys Ala Leu Asp Thr Val Gly Trp Val Gln Arg His Arg Lys
    50                  55                  60

Met Leu Arg His Cys Pro Ser Lys Arg Lys
65                  70

<210> SEQ ID NO 31
<211> LENGTH: 70
<212> TYPE: PRT
<213> ORGANISM: Escherichia coli

<400> SEQUENCE: 31

Ala Ser Leu Ala Ala Asp Thr Pro Thr Ala Cys Cys Phe Ser Tyr Thr
1               5                   10                  15

Ser Arg Gln Ile Pro Gln Asn Phe Ile Ala Asp Tyr Phe Glu Thr Ser
            20                  25                  30

Ser Gln Cys Ser Lys Pro Gly Val Ile Phe Leu Thr Lys Arg Ser Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70

<210> SEQ ID NO 32
<211> LENGTH: 68
<212> TYPE: PRT
<213> ORGANISM: Escherichia coli

<400> SEQUENCE: 32

Ser Phe His Phe Ala Ala Asp Cys Cys Thr Ser Tyr Ile Ser Gln Ser
1               5                   10                  15

Ile Pro Cys Ser Leu Met Lys Ser Tyr Phe Glu Thr Ser Ser Glu Cys
            20                  25                  30

Ser Lys Pro Gly Val Ile Phe Leu Thr Lys Lys Gly Arg Gln Val Cys
        35                  40                  45

Ala Lys Pro Ser Gly Pro Gly Val Gln Asp Cys Met Lys Lys Leu Lys
    50                  55                  60

Pro Tyr Ser Ile
65

<210> SEQ ID NO 33
<211> LENGTH: 68
<212> TYPE: PRT
<213> ORGANISM: Escherichia coli

<400> SEQUENCE: 33

Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
            20                  25                  30

Cys Pro Lys Leu Gly Val Ile Leu Leu Thr Lys Arg Gly Arg Gln Ile
        35                  40                  45

Cys Ala Asp Pro Asn Lys Lys Trp Val Gln Lys Tyr Ile Ser Asp Leu
    50                  55                  60

Lys Leu Asn Ala
65

<210> SEQ ID NO 34
<211> LENGTH: 76
<212> TYPE: PRT
<213> ORGANISM: Escherichia coli

<400> SEQUENCE: 34

Asp Arg Phe His Ala Thr Ser Ala Asp Cys Cys Ile Ser Tyr Thr Pro
1               5                   10                  15

Arg Ser Ile Pro Cys Ser Leu Leu Glu Ser Tyr Phe Glu Thr Asn Ser
            20                  25                  30

Glu Cys Ser Lys Pro Gly Val Ile Phe Leu Thr Lys Lys Gly Arg Arg
        35                  40                  45

Phe Cys Ala Asn Pro Ser Asp Lys Gln Val Gln Val Cys Met Arg Met
    50                  55                  60

```
Leu Lys Leu Asp Thr Arg Ile Lys Thr Arg Lys Asn
 65                  70                  75

<210> SEQ ID NO 35
<211> LENGTH: 74
<212> TYPE: PRT
<213> ORGANISM: Escherichia coli

<400> SEQUENCE: 35

Thr Lys Thr Glu Ser Ser Arg Gly Pro Tyr His Pro Ser Glu Cys
 1               5                  10                  15

Cys Phe Thr Tyr Thr Thr Tyr Lys Ile Pro Arg Gln Arg Ile Met Asp
                20                  25                  30

Tyr Tyr Glu Thr Asn Ser Gln Cys Ser Lys Pro Gly Ile Val Phe Ile
             35                  40                  45

Thr Lys Arg Gly His Ser Val Cys Thr Asn Pro Ser Asp Lys Trp Val
     50                  55                  60

Gln Asp Tyr Ile Lys Asp Met Lys Glu Asn
 65                  70

<210> SEQ ID NO 36
<211> LENGTH: 96
<212> TYPE: PRT
<213> ORGANISM: Escherichia coli

<400> SEQUENCE: 36

Pro Lys Val Pro Glu Trp Val Asn Thr Pro Ser Thr Cys Cys Leu Lys
 1               5                  10                  15

Tyr Tyr Glu Lys Val Leu Pro Arg Arg Leu Val Val Gly Tyr Arg Lys
                20                  25                  30

Ala Leu Asn Cys His Leu Pro Ala Ile Ile Phe Val Thr Lys Arg Asn
             35                  40                  45

Arg Glu Val Cys Thr Asn Pro Asn Asp Asp Trp Val Gln Glu Tyr Ile
     50                  55                  60

Lys Asp Pro Asn Leu Pro Leu Leu Pro Thr Arg Asn Leu Ser Thr Val
 65                  70                  75                  80

Lys Ile Ile Thr Ala Lys Asn Gly Gln Pro Gln Leu Leu Asn Ser Gln
                85                  90                  95

<210> SEQ ID NO 37
<211> LENGTH: 76
<212> TYPE: PRT
<213> ORGANISM: Escherichia coli

<400> SEQUENCE: 37

Gln Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
             35                  40                  45

Lys Glu Val Cys Ala Asp Pro Lys Glu Arg Trp Val Arg Asp Ser Met
     50                  55                  60

Lys His Leu Asp Gln Ile Phe Gln Asn Leu Lys Pro
 65                  70                  75

<210> SEQ ID NO 38
<211> LENGTH: 69
<212> TYPE: PRT
```

-continued

```
<213> ORGANISM: Escherichia coli

<400> SEQUENCE: 38

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
                20                  25                  30

Ser Leu Cys Ser Gln Pro Ala Val Val Phe Gln Thr Lys Arg Ser Lys
            35                  40                  45

Gln Val Cys Ala Asp Pro Ser Glu Ser Trp Val Gln Glu Tyr Val Tyr
        50                  55                  60

Asp Leu Glu Leu Asn
65

<210> SEQ ID NO 39
<211> LENGTH: 5
<212> TYPE: PRT
<213> ORGANISM: Artificial
<220> FEATURE:
<223> OTHER INFORMATION: synthetic

<400> SEQUENCE: 39

Lys Lys Trp Val Arg
1               5

<210> SEQ ID NO 40
<211> LENGTH: 7
<212> TYPE: PRT
<213> ORGANISM: Artificial
<220> FEATURE:
<223> OTHER INFORMATION: synthetic

<400> SEQUENCE: 40

Met Lys Lys Lys Trp Pro Arg
1               5
```

CHEMOKINE MUTANTS IN THE TREATMENT OF MULTIPLE SCLEROSIS

FIELD OF THE INVENTION

The present invention relates to mutants of CC chemokines, which contain at least two mutations in the 40's loop and which, relative to the wild-type molecule, have a reduced GAG-binding activity: it has been found that such mutated chemokines are effective in the treatment of multiple sclerosis and/or other demyelinating diseases.

BACKGROUND OF THE INVENTION

Chemokines constitute a family of small pro-inflammatory cytokines with leukocyte chemotactic and activating properties. Depending on the position of the first conserved cysteines, the chemokine family can be divided in C—C, C—X—C and C—X$_3$—C chemokines (Baggiolini M. et al., Adv Immunol. 1994, 55:97-179; Baggiolini M. et al., Annu Rev Immunol. 1997,15:675-705; Taub D. et al., Cytokine Growth Factor Rev. 1996,7(4):355-76).

Many C—X—C chemokines such as interleukin-8 (IL-8) are chemotactic for neutrophils, while C—C chemokines are active on a variety of leukocytes including monocytes, lymphocytes, eosinophils, basophils, NK cells and dendritic cells.

The NH$_2$-terminal domain of chemokines is involved in receptor binding and NH$_2$-terminal processing can either activate chemokines or render chemokines completely inactive.

N-terminal variants of synthetical C—C chemokines have been tested for their activity as inhibitors or antagonists of the naturally occurring forms. MCP-1, MCP-3 and RANTES missing the 8 to 9 NH$_2$-terminal amino acids are inactive on monocytes and are useful as receptor antagonists (Gong J H et al., J Exp Med. 1995,181(2):631-40 and Gong J H et al., J Biol Chem. 1996, 271(18):10521-7).

Extension of RANTES with one methionine results in almost complete inactivation of the molecule and Met-RANTES behaves as an antagonist for the authentic one (Proudfoot A E et al., J Biol Chem. Feb. 2, 1996;271 (5):2599-603).

WO 99/16877 relates to amino-terminally truncated RANTES, lacking NH$_2$-terminal amino acids corresponding to amino acid residues 1, 1-2, 1-3 or 1-4 of the naturally-occurring RANTES and having chemokine antagonistic activity, as well as cDNA sequences encoding them, their use in therapy and/or in diagnosis of the diseases, in which an antagonistic activity of the chemokine effects is required. RANTES (3-68) is the preferred truncated chemokine antagonist.

Even if the chemoattractant activity of RANTES and of CC chemokines in general has been studied mainly in connection with the specific cell membrane receptors, RANTES can interact also with Glycosaminoglycans (GAGs), highly variable, branched sugar groups added post-translationally to several proteins, generically called proteoglycans (PGs). Such proteins are present on cell membrane, in the extracellular matrix and in the blood steam, where isolated GAGs can also be present.

The interaction with GAGs is a feature common to many cel-signaling soluble molecules (interleukins, growth factors). PGs, or isolated GAGs, can form a complex with soluble molecules, probably at the scope to protect this molecule from proteolysis in the extracellular environment It has been also proposed that GAGs may help the correct presentation of cell signaling molecules to their specific receptor and, eventually, also the modulation of target cell activation.

In the case of chemokines, the concentration into immobilized gradients at the site of inflammation and, consequently, the interaction with cell receptors and their activation state seem to be modulated by the different forms of GAGs (Hoogewerf A J et al., Biochemistry 1997, 36(44):13570-8). Therefore, it has been suggested that the modulation of the such interactions may represent a therapeutic approach in inflammatory disease (Schwarz M K and Wells TN, Curr Opin Chem Biol. 1999, 3(4):407-17) and in HIV infection (Bums J M et al., Proc Natl Acad Sci U.S.A. 1999, 96(25): 14499-504).

The structural requirements and functional effects of GAG-RANTES interaction have been studied in various models. RANTES binds GAGs on human umbilical vein endothelial cells (HUVECs) at micromolar concentrations with an affinity and a specificity higher then other chemokines, like MCP-1, IL-8, or MIP-1 alpha. Such interaction appears to be not simply electrostatic but also depending by other parameters like length and N- and O-sulfation of the GAGs (Kuschert G S et al., Biochemistry 1999, 38(39):12959-68). GAG-defective cell lines still can bind chemokines but the presence of cell surface GAGs greatly enhances their activity on the receptors when they are at low concentrations (Ali S et al., J Biol Chem 2000, 275(16): 11721-7). Other experiments showed that GAGs, heparin sulphate in particular, facilitate the interaction of RANTES with the cell surface of macrophages and the consequent inhibition of HIV infection, a result consistent with the well-known resistance of these cells, poorly expressing heparin sulphate, to antiviral effects of RANTES (Oravecz T, et al., J Immunol. 1997,159(9):4587-92).

Soluble GAGs compete with cell membrane GAGs, and they can act as specific inhibitors of RANTES-induced activation surface (Appay V, et al.; Int Immunol 2000, 12(8): 11737-82), or as suppressor HIV infection (Bums J M, et al.; Proc Natl Acad Sci U.S.A. 1999, 96(25):14499-504).

Some structure-function studies tried to identify the RANTES domain responsible of the interaction with GAGs, since the traditional consensus sequence (BBXB, where B is a basic residue and X can be any residue) is too generic. An epitope-mapping study was performed by using a monoclonal antibody, raised against recombinant human RANTES, capable to block both the antiviral effects and the mobilization of intracellular calcium mediated by RANTES (Bums J M et al., J. Exp . Med. 1998, 188(10):1917-27). This approach allowed to define the residues 55-66 as necessary both for such activities and for GAG interaction, arguing that GAGs interaction may have a complementary or distinct function from the one mediated by canonical receptors, as also suggested in a study on RANTES variants having altered aggregation properties (Appay V et al., J Biol Chem 1999, 274(39):27505-12).

The region 55-66, which represents the C-terminal alpha-helical segment, is homologous to the GAG-binding domain of other chemokines, like IL-8 (Witt DP and Lander AD, Curr. Biol. 1994, 4(5):394-400), and contains a cationic site containing lysine and arginine (KKWVR) (SEQ ID NO: 39). Such binding region is distinct from the binding site for cell receptors, which is located at the N-terminus (Pakianathan DR et al., Biochemistry 1997, 36(32): 9642-8), and contains some residues involved in the aggregation of RANTES monomers, even though such disaggregating mutations seem not to affect the interaction with GAGs (Czaplewski L. G. et al., J. Biol. Chem. 1999, 274(23): 1607784; WO 98/13495).

RANTES contains another cationic site (RKNR) at residues 44-47 which is conserved in the GAG binding domain of other chemokines, like MIP-1α (Koopmann W and Krangel MS; J. Biol. Chem. 1997, 272(15):10103-9) and MIP-1β (Koopmann W et al., J Immunol. 1999, 163(4):2120-7).

Human RANTES variants containing single mutations in these cationic sites have been disclosed as RANTES antagonists having potential therapeutic applications in the treatment of HIV infection and inflammatory or allergic diseases (WO 99/33989).

It has also been disclosed that only a triple mutant of RANTES, in which three residues at positions 44, 45 and 47 have been substituted with Alanine, has lost the GAG-binding ability (A Proudfoot et al., Chemokine Gordon Conference, Session I, Jul. 24, 2000, personal communication).

DESCRIPTION OF THE INVENTION

It has now been found that CC chemokines, containing at least two mutations in the cationic site of the so-called "40's loop" are effective in the treatment of multiple sclerosis and/or other demyelinating diseases. This site represents a conserved GAG-binding motif in the CC chemokines (like RANTES, MIP-1alpha and MIP-1beta, MIP-3, MIP-4, HCC1, I309, MCP-2). All these chemokine mutants have a reduced GAG-binding activity, when compared to the wild-type corresponding molecules.

The region in which at least two mutations should be present according to the invention, the so-called 40's loop, is indicated for a number of CC chemokines in FIG. 1. In particular, RANTES triple mutant, in which three basic residues at positions 44, 45 and 47 have been substituted with Alanine, has been found to be active in an animal model for the treatment of multiple sclerosis. This triple mutant of RANTES showed a dose-related effect in the murine EAE model and a comparable efficacy to the reference treatment with recombinant IFN-beta. Analogous results have been found with a truncated RANTES triple mutant, in which three residues at positions 44, 45 and 47 have been substituted with Alanine and which lacks the first 2 N-terminal amino acids. This truncated RANTES mutant (having the amino acid sequence of SEQ ID NO: 2) is novel and represents another object of the present invention.

Similar experimental evidence have also been generated in connection with triple mutants of MIP-1alpha and MIP-1beta, which are already known and which are herein identified as MIP-1α triple mutant R18A-R46A-R48A (Koopmann W and Krangel M S., J Biol Chem. 1997, 272(15):10103-9) and MIP-1β triple 40's mutant K45A-R46A-K48A (Laurence JS, Biochemistry 2001, 40:4990-4999).

The wording "a reduced GAG-binding activity" means that the mutants of the invention have a lower ability to bind to GAGs, i.e. a lower percentage of each of these mutants bind to GAGs (like heparin sulphate) with respect to the corresponding wild-type molecule.

More preferably are mutants of human RANTES, in which the three basic amino acids at positions 44, 45 and 47 of the wild-type molecule have been substituted by other amino acids. Such residues can be substituted with small, aliphatic, non-polar or slightly polar residues, such as for example Ala, Ser, Thr, Pro, and Gly. Alanine is the preferred one.

RANTES mutants that have been found to be particularly effective in the treatment of MS are those having the amino acid sequences as reported in SEQ ID NO: 2 and SEQ ID NO: 3 respectively.

Another object of the present invention is the use the chemokine mutants as above defined to produce a pharmaceutical composition for treating multiple sclerosis and/or other demyelinating diseases.

Multiple sclerosis (MS) is a slowly progressive CNS disease characterized by disseminated patches of demyelination in the brain and spinal cord, resulting in multiple and varied neurologic symptoms and signs, usually with remissions and exacerbation (see The Merck Manual, sixteenth edition).

The cause is unknown but an immunologic abnormality is suspected, with few clues presently indicating a specific mechanism. Postulated causes include infection by a slow or latent virus, and myelinolysis by enzymes. IgG is usually elevated in the CSF, and elevated titers have been associated with a variety of viruses, including measles. The significance of these findings and of reported associations with HLA allotypes and altered number of T cells is unclear, since evidences are somewhat conflicting. An increased family incidence suggests genetic susceptibility; women are somewhat more often affected than men are. Environmental factors seem to be present. Although age at onset generally is from 20 to 40 years, MS has been linked to the geographic area where a patient's first 15 years are spent. Relocation after age 15 does not alter the risk.

Plaques or islands of demyelination with destruction of oligodendroglia and perivascular inflammation are disseminated through the CNS, primarily in the white matter, with a predilection for the lateral ad posterior columns (especially in the cervical and dorsal regions), the optic nerves, and periventricular areas. Tracts in the midbrain, pon, and cerebellum also are affected, and gray matter in both cerebrum and cord may be affected.

Cell bodies and axons are usually preserved, especially in early lesions. Later, axons may be destroyed, especially in the long tracts, and a fibrous gliosis gives the tracts their "sclerotic" appearance. Both early and late lesions may be found simultaneously. Chemical changes in lipid and protein constituents of myelin have been demonstrated in and around the plaques.

The disease is characterized by various complaints and findings of CNS dysfunction, with remissions and persistently recurring exacerbations.

Magnetic Resonance Imaging (MRI) is the most sensitive diagnostic imaging technique; it may show many plaques. Lesions also may be visible on contrast-enhanced CT scans.

Therapeutic advances in multiple sclerosis (MS) have been slow to emerge, partly because of incomplete understanding of the pathogenesis of the disorder. For empirically based treatment the major obstacles to progress include the highly variable course of MS, the long-term nature of the most important outcome measures, and the lack of objective markers of treatment effect, particularly in the short term.

Although the pathogenesis of MS remains uncertain, the natural history continues to be studied. Objective outcome measures based on magnetic resonance imaging (MRI) have been developed and many of the pitfalls of dinical trials are now known, which has led to improved trial methods and better interpretation of results.

Another object of the present invention is, therefore, the method for treating MS by administering an effective amount of the chemokine mutants of the invention together with a pharmaceutically acceptable excipient An "effective amount" refers to an amount of the active ingredients that is sufficient to affect the course and the severity of the disease, leading to the reduction or remission of such pathology. The effective amount will depend on the route of administration and the condition of the patient.

A further object of the present invention are the pharmaceutical compositions containing the chemokine mutants of the invention, in the presence of one or more pharmaceutically acceptable excipients, for treating MS and/or other demyelinating diseases.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringers solution.

Besides the pharmaceutically acceptable carrier, the compositions of the invention can also comprise minor amounts of additives, such as stabilizers, excipients, buffers and preservatives.

The administration of such active ingredient may be by intravenous, intramuscular or subcutaneous route. Other routes of administration, which may establish the desired blood levels of the respective ingredients, are comprised by the present invention.

The optimal dose of active ingredient may be appropriately selected according to the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

Usually a daily dosage of active ingredient can be about 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

DESCRIPTION OF THE FIGURES

FIG. 10: it shows the inhibition of thioglycollate induced cellular recruitment by the triple 40's RANTES mutant.

EXAMPLES

Figure 1:
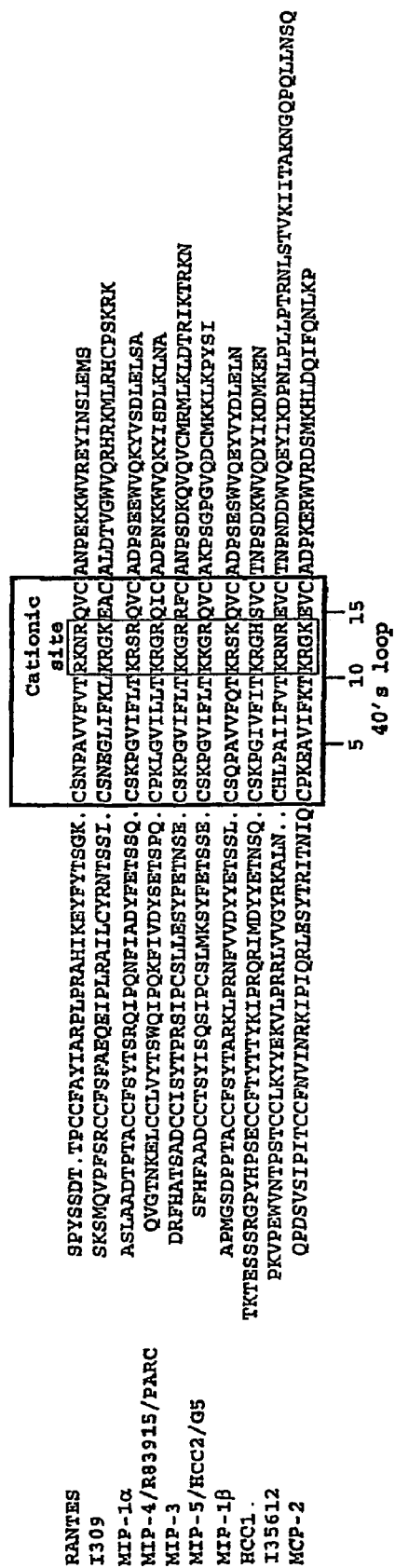
FIG. 1: it represents an alignment of some exemplary CC Chemokines, RANTES (corresponding to residues 24-91 of SEQ ID NO:1); I309 (SEQ ID NO:30); MIP-1α (SEQ ID NO:31); MIP-4/R83915/PARC (SEQ ID NO:33); MIP-3 (SEQ ID NO:34); MIP-5/HCC2/G5 (SEQ ID NO:32); MIP-1β (SEQ ID NO:38); HCC1 (SEQ ID NO:35); I35612 (SEQ ID NO:36); and MCP-2 (SEQ ID NO:37) aligned at the level of the 40's loop. This protein segment and the cationic site which corresponds to the GAG-binding motif are boxed.

1. Materials and Methods a) Generation of Non-Heparin Binding RANTES Mutants

Mutagenesis of RANTES was achieved by an inverse polymerase chain reaction technique. The point mutations were introduced into one of the two primers used to hybridise to human RANTES coding sequence (GenBank acc. No. NM_002985) in the opposite orientation. In order to improve the efficiency of primer annealing (especially when multiple mutations were introduced into primers) the DNA was alkali-denatured. The denatured DNA was diluted to a concentration of approximately 10 pg/reaction to avoid the incorporation of unmutated DNA into the transformation reaction.

The amino acids numbering given in the Examples and in the Description considers the mature protein, i.e. as starting with Ser, which is the amino acid at position 24 according to the Sequence Listing. Therefore to have a perfect correspondence between the amino acids numbers in the Sequence Listing and that in the Examples, 23 should be added to the numbers appearing in the Examples or in the Description.

The sequences of mutagenic primers used are as follows and the mutated bases are underlined:

```
R44A (sense)
5'-TTTGTCACCGCAAAGAACCGCCAAG-3':        P1 (SEQ ID NO:14)

R44A (anti-sense)
5'-GACGACTGCTGGGTTGGAGCACTTG-3':        P2 (SEQ ID NO:15)

K45A (sense)
5'-TTTGTCACCCGAGCGAACCGCCAAG-3':        P3 (SEQ ID NO:16)
```

-continued

```
K45A (anti-sense)
5'-GACGACTGCTGGGTTGGAGCACTTG-3':                        P4  (SEQ ID NO:17)

R47A (sense)
5'-CGAAAGAACGCCCAAGTGTGTGCCA-3':                        P5  (SEQ ID NO:18)

R47A (anti-sense)
5'-GGTGACAAAGACGACTGCTGGGTTG-3':                        P6  (SEQ ID NO:19)

R44A-K45A-R47A (triple 40's mutant, sense)
5'-TTTGTCACCGCAGCGAACGCCCAAGTGTGTGCCAAC-3':             P7  (SEQ ID NO:20)

R44A-K45A-R47A (triple 40's mutant, anti-sense)
5'-GACGACTGCTGGGTTGGAGCACTTGCC-3':                      P8  (SEQ ID NO:21)

K55A (sense)
5'-GCCAACCCAGAGGCGAAATGGGTTCGG-3':                      P9  (SEQ ID NO:22)

K55A (anti-sense)
5'-ACACACTTGGCGGTTCTTTCGGGTGAC-3':                      P10 (SEQ ID NO:23)

K56A (sense)
5'-AACCCAGAGAAGGCATGGGTTCGGGAG-3':                      P11 (SEQ ID NO:24)

K56A (anti-sense)
5'-GGCACACACTTGGCGGTTCTTTCGGGT-3':                      P12 (SEQ ID NO:25)

R59A (sense)
5'-AAGAAATGGGTTGCGGAGTACATCAAC-3':                      P13 (SEQ ID NO:26)

R59A (anti-sense)
5'-CTCTGGGTTGGCACACACTTGGCG-3':                         P14 (SEQ ID NO:27)

K55A-K56A-R59A (triple 50's mutant, sense)
5'-GCCAACCCAGAGGCGGCATGGGTTGCGGAGTACATC-3':             P15 (SEQ ID NO:28)

K55A-K56A-R59A (triple 50's mutant, anti-sense)
5'-ACACACTTGGCGGTTCTTTCGGGTGACAAAGAC-3':                P16 (SEQ ID NO:29)
```

Amplification was performed in a DNA thermal cycler (Perkin-Elmer-Cetus 480) for 35 cycles using pfuturbo® DNA polymerase (Stratagene). DNA was ligated and transformed into Top 10 F' competent *E. coil* cells (Invitrogen). The sequence of the mutants was verified by DNA sequencing.

b) Expression and Purification of Wild-Type (WT) RANTES and RANTES Mutants in *E. coli*

Figure 2:
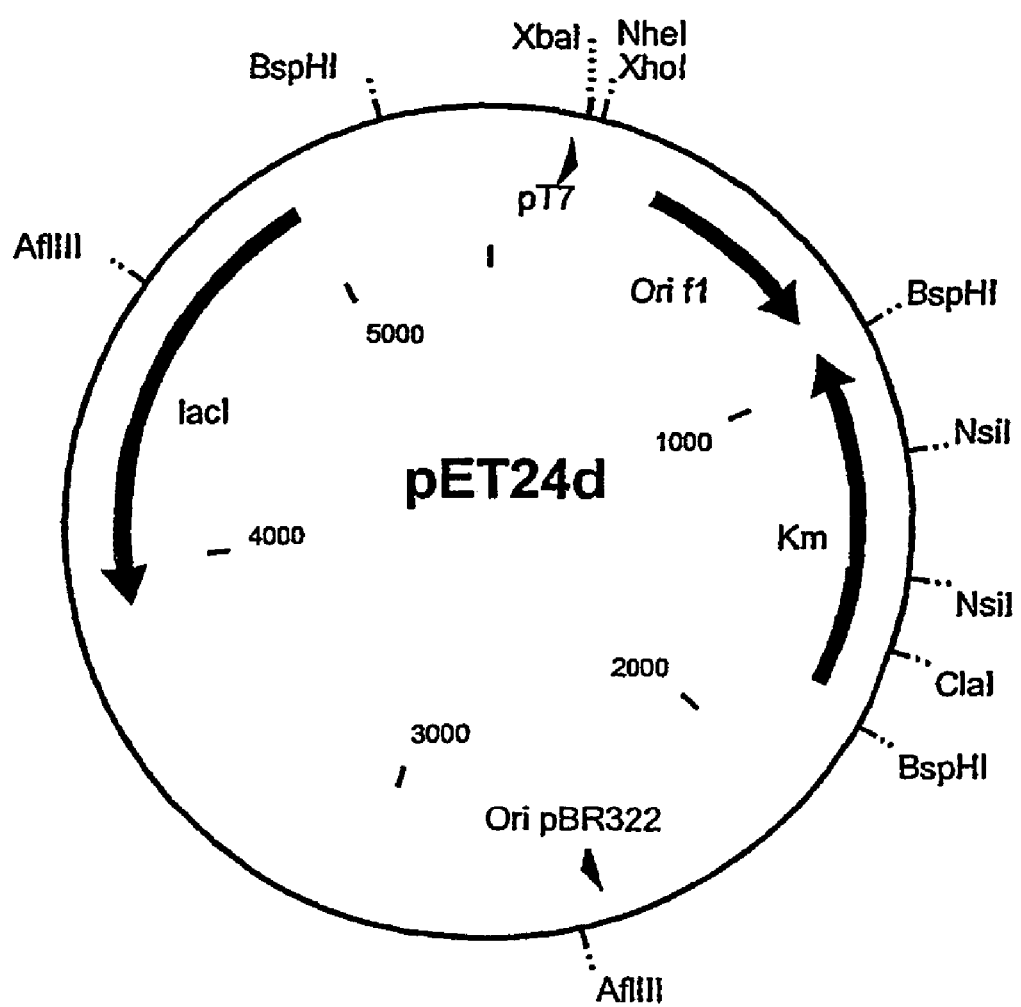
FIG. 2: it shows the map of the plasmid used to clone Wild Type RANTES and its mutants according to the Examples.

The DNA fragments obtained by PCR as above explained and have been cloned into the plasmid pET24d (FIG. 2), generating a series of vectors. WT or mutated RANTES coding sequence is cloned in 3' to the pT7 promoter, between the XbaI and NheI/XhoI sites. The plasmid contains two marker genes (Km and lacI) and an active replication origin (Ori fl).

The resulting vectors were used to retransform the BL21 (DE3) *E.coli* strain, which allows strong protein expression using the pT7/LacI system. Protein expression was induced by addition of 1 mM isopropyl-β-D-thiogalactopyranoside (IPTG) to the culture. Cells were harvested and resuspended in lysis buffer (50 mM Tris-HCl pH 8, 10 mM $MgCl_2$, 5 mM Benzamidine/HCl, 1 mM DTT, 0.1 mM phenylmethylsulfonyl fluoride (PMSF), DNase 20 mg/L). Cells were broken by three passages through the French Pressure Cell unit. The suspension was then centrifuged at 10,000×g for 30 min at 4° C. The inclusion body pellet containing the WT RANTES or one of the RANTES mutants was solubilised in 0.1 M Tris/HCl, pH 8,0, containing 6M Guanidine/HCl, and 1 mM DTT and stirred for 30 min at 60° C. The solution was dialysed against 3 changes of 1% acetic acid. Insoluble material was removed by centrifugation at 10,000×g for 30 min. The supernatant containing the WT RANTES or one of the RANTES mutants was lyophilised.

The lyophilised powder was dissolved in 0.1 M Tris/HCl, pH 8,0, containing 6M Guanidine/HCl, and 1 mM DTT to obtain a concentration of approximately 1 mg/ml. The proteins were renatured by dropwise dilution into a volume 10× that of the guanidine solution of 20 mM Tris/HCl, pH 8.0 containing 0.01 mM oxidised glutathione and 0.1 mM reduced glutathione. The solution was stirred overnight at 4° C. Insoluble material was removed by centrifugation 10,000×g for 30 min. The pH was adjusted to 4.5 with acetic acid, and the conductivity adjusted to 20 mS by dilution with water. The solution was applied to a HiLoad S 26/10 column previously equilibrated in 20 mM sodium acetate, pH 4.5, and protein was eluted with a linear 0-2 M NaCl gradient in the same buffer. The fractions containing WT RANTES or one of the RANTES mutant proteins were pooled, dialysed against 3 changes of acetic acid, and lyophilised.

The lyophilised proteins were dissolved in 50 mM Tris/HCl buffer, pH 8.0. The MKKKWPR (SEQ ID NO:40) leader sequence derived from the cloning procedure was cleaved from WT RANTES or one of the RANTES mutant proteins by incubation with endoproteinase Arg-C (1:600 enzyme: substrate, w/w) overnight at 37° C. The cleaved proteins were separated from uncleaved protein by cation exchange chromatography on a HiLoad S 26/10 column previously equilibrated in 20 mM sodium acetate, pH 4.5, containing 6 M urea, and proteins were eluted with a linear 0-2M NaCl gradient in the same buffer. The cleaved fractions were pooled and dialysed against two changes of 1% acetic acid, and finally against 0.1% trifluoroacetic acid, and then lyophilised (Edgerton MD et al., pg. 33-40, and and Proudfoot AE et al., pg. 75-87, in "Chemokine Protocols", Methods in Molecular Biology 2000, vol.138, Humana Press).

The authenticity of the WT and RANTES mutant proteins was verified by mass spectrometry. With an analogous procedure another mutant has been produced which contained a Met, as $NH_2$-terminus extension, as well as the single or triple 40's RANTES mutants and the single or triple 50's mutants.

c) Expression and Purification of Wild-Type (WT) RANTES and RANTES Mutants in *Pichia pastoris*

The mature triple 40's RANTES mutant (R44A-K45A-R47A) was created using megaprimer based PCR mutagenesis (Datta A K, Nucleic Add Research 1995, 23(21):4530-31). It was cloned into the *Pichia pastodis* expression vector, pPIC9K, in frame with *S. cerevisiae* Mat alpha pre-pro signal peptide.

After sequence confirmation, the plasmid was transferred into *Pichia pastolis* host strain GS115(his4) by electroporation. His+ clones were screened for the expression of the RANTES mutant The small-scale expression studies were carried out using standard procedures as described in the Pichia Expression Kit from Invitrogen (Life Technologies). Briefly, the culture was expanded in an enriched medium using glycerol as a carbon source, after which it was pelleted down and resuspended in medium containing methanol to induce the expression of the RANTES mutant protein. The secretion of the RANTES mutant in the medium was detected on Coomassie Blue stained SDS-PAGE.

A clone secreting high levels of RANTES mutant (approx. 500-750 mg/l) was used for scale up in large shake flasks. The fermented broth was centrifuged at 5,000 rpm and the supernatant used for purification.

The protein was purified from the supernatant by a single chromatographic step on a Heparin Sepharose column, equilibrated in 0.1 M Tris-HCl, and eluted with a linear gradient of 0-2 M NaCl in the same buffer using 20 column volumes. The authenticity of the protein was verified by mass spectrometry and it was discovered that in such system the RANTES mutant (R44A-K45A-R47A) so produced is also truncated at the N-terminus with respect to the wild type molecule, i.e. it lacks the first 2 amino acids. The mutant so obtained has therefore been identified as triple 40's RANTES (368) mutant (R44A, K45A, R47A) and has amino acid sequence is that of SEQ ID NO: 3.

d) Heparin Binding Assays

Heparin sepharose chromatography was performed using 50 μg WT or mutated RANTES proteins which were loaded onto a Heparin Sepharose column equilibrated in 25 mM Tris/HCl, pH 8.0 and 50 mM NaCl and eluted with a linear gradient of 0-2 M NaCl in 25 mM Tris/HCl, pH 8.0.

Heparin sepharose chromatography was performed using 50 μg WT or mutated RANTES proteins which loaded onto a MonoS cation exchange column equilibrated in 50 mM sodium acetate, pH 4.5. Protein was eluted with a 0-2 M NaCl gradient.

Competition binding assay was performed using WT RANTES, triple 50's RANTES mutant, and triple 40's RANTES mutant (SEQ ID NO:3- also identified herein as "R44A-K45A-R47A RANTES") which were radiolabelled with $^{125}$I by Amersham to a specific activity of 2200 mCi/mole. Filter plates having 96 wells were soaked with binding buffer (50 mM HEPES, pH 7.2 containing 1 mM $CaCl_2$, 5 mM $MgCl_2$, 0.15 M NaCi and 0.5% BSA). Serial dilutions of heparin in the binding buffer were carried out to cover the concentration range from 20 mg/ml to 1 μg/ml. The assay was performed in a total volume of 100 μl by adding 25 μl of the heparin dilutions, 25 μl of 0.4 nM [$^{125}$I]-chemokine, 25 μl of heparin beads (0.2 μg/ml in water) and 25 μl of binding buffer to each well. The assays were carried out in triplicate. The plates were incubated at room temperature with agitation for 4 hours. The filter plates were washed 3 times with 200 μl of washing buffer using a vacuum pump to remove unbound-labelled chemokine. Then 50 μl of scintillant was added to each well and radioactivity counted (1 mm/well). Data were analysed using GraFit Software.

e) Equilibrium Competition Receptor Binding Assays

The assays were carried out on membranes from CHO transfectants expressing CCR1 or CCR5 using a Scintillation Proximity Assay (SPA) using [$^{125}$I]-MIP-1α as tracer. Competitors were prepared by serial dilutions of the unlabelled chemokines in binding buffer to cover the range $10^{-6}$-$10^{-12}$ M. The binding buffer used was 50 mM HEPES, pH 7.2 containing 1 mM $CaCl_2$, 5 mM $MgCl_2$, 0.15 M NaCl and 0.5% BSA. Wheatgerm SPA beads (Amersham) were solubilised in PBS to 50 mg/ml, and diluted in the binding buffer to a 10 mg/ml, and the final concentration in the assay was 0.25 mg/well. Membranes prepared from CHO cells expressing CCR1 or CCR5 were stored at −80° C. and diluted in the binding buffer to a 80 μg/ml. Equal volumes of membrane and beads stocks were mixed before performing the assay to reduce background. The final membrane concentration was 2 μg/ml and that of [$^{125}$I]-MIP-1α was 0.1 nM. The plates were incubated at room temperature with agitation for 4 hours. Radioactivity was measured and data analysed as described for the heparin-binding assay.

f) Chemotaxis Assays

Monocyte chemotaxis was carried out using the micro-Boyden chamber assay. Monocytes were purified from buffy coats using the following isolation procedure: 100 ml of buffy coat solution was diluted with 100 ml of PBS, layered on Ficoll and centrifuged at 600×g for 20 min at room temperature. The cells forming the interface were collected, washed twice with PBS, and resuspended at a concentration of 40-100×$10^6$/ml in RPMI 1640 medium containing 5% inactivated fetal calf serum (FCS), 2 mM glutamine and 25 mM HEPES, pH 7.2. They were further purified from the lymphocyte fraction by adding $10^6$ sheep red blood cells/ml, rosetted overnight at 4° C., and separated by a second Ficoll gradient centrifugation at 900×g for 20 min at room temperature. The monocytes were found in the interface between the Ficoll and the buffer, and the T cells were in the pellet The monocytes were washed in PBS and resuspended at 2.5×$10^6$/ml in RPMI 1640 medium. The purity was measured by forward and side scatter by FACS analysis, and was found to be 40-80% depending on the donor Chemokine were diluted to a final volume of 30 μl, covering the concentration range of $10^{-6}$-$10^{-12}$ M in RPMI medium was placed in the lower wells. A filter with 5 μm pore size (Neuroprobe) for monocytes and 8 μm for T cells was placed over the lower wells ensuring that there are no air bubbles, and the system sealed. Fifty microliters of the cell suspension (2.5×$10^6$ cells/ml) in RPMI medium was placed in the upper wells. The chamber was incubated for 30 minutes for monocytes and 1.5 hours for T cells at 37° C. under $O_2$. The cells were then discarded, the upper surface of the membrane scraped clean of cells, and the membrane then washed with PBS. The membrane was fixed by immersion in MeOH for 1 minute, air dried and stained with Fields A and B solutions. Migrated cells were counted by selecting random fields for each well with a 20× objective on a standard microscope fitted with IBAS image analyser software. The data were fitted using GraFit software.

g) Peritoneal Cellular Recruitment Assays

In a first assay, cellular recruitment was induced by intraperitoneal injection of 10 μg of the chemokine diluted in 0.2-ml sterile saline (LPS-free NaCl) into female BALB/c mice of 8 to 12 wks of age. The chemokine mutants (10 μg of the chemokine diluted in. 0.2 ml sterile saline) were administered 30 min prior to the agonist administration. Sixteen hours later, mice were sacrificed by aerosolized $CO_2$. Peritoneal lavage was performed with 3 washes with 5 ml PBS, and the lavages pooled. Cells were centrifuged at 600×g for 10 min, resuspended in a final volume of 1 ml and total leukocytes elicited were counted with a hemacytometer.

In a second assay, cellular recruitment was induced by intraperitoneal injection of 200 μl of a 3% solution of thioglycollate in distilled water into female BALB/c mice of 8 to 12 wk of age (Day 1). The chemokine mutant (10 μg of the chemokine diluted in 0.2 ml sterile saline) was administered 30 min prior to the thioglycollate administration. The chemokine mutant was administered daily thereafter for 3 days (Day 2, 3 and 4). The mice were sacrificed on Day 5 by aerosolised $CO_2$. Peritoneal lavage was performed with 3 washes with 5 ml PBS, and the lavages pooled. Cells were centrifuged at 600×g for 10 min, resuspended in a final volume of 1 ml and total leukocytes elicited were counted with an haemocytometer.

h) Experimental Autoimmune Encephalomyelitis (EAE)

Immunization Procedure 8-week old C57 BL/6NCrlBR female mice weighing 18-22 grams were immunized (day=0) by injecting s.c. in the back of the neck 0.1 ml of an emulsion containing 200 μg $MOG_{35-55}$ peptide (Neosystem, Strasbourg, France) in Complete Freund's Adjuvant (CFA with *Mycobactedum butyricum*, Difco, Detroit, U.S.A.) containing 0.25 mg of *Mycobacterium tuberculosis*. Before the s.c injection, they received a 200 μl i.v. injection of 300 ng pertussis toxin (List Biological Lab., Campbell, Calif., U.S.A) dissolved in PBS in the tail vein. On day 2 the animals were given a second i.p. injection of 300 ng of pertussis toxin.

This procedure results, starting approximately from day 8-10, in the appearance of a progressive paralysis, arising from the tail and progressively ascending up to the forelimbs.

Study Design

The study involved groups of 10 animals each. All the groups were immunized with $MOG_{35-55}$ peptide in CFA and pertussis toxin, according with the immunization protocol.

| Group 1: | positive control group dosed with vehicle alone (PBS) by i.p. route. |
|---|---|
| Group 2: | positive control group dosed with vehicle alone (PBS) by s.c. route. |
| Group 3: | dosed with 10 μg/mouse i.p. of triple 40's RANTES mutant |
| Group 4: | dosed with 1 μg/mouse i.p. of triple 40's RANTES mutant |
| Group 5: | dosed with 10 μg/mouse i.p. of triple 40's Met-RANTES mutant |
| Group 6: | dosed with 1 μg/mouse i.p. of triple 40's Met-RANTES mutant |
| Group 7: | dosed with 10,000 U/mouse s.c. of mouse recombinant interferon beta (m-IFN-β) |
| Group 8: | dosed with 20,000 U/mouse s.c. of m-IFN-β |

Vehicle

PBS was used to dilute RANTES all 40's triple mutant, Met-RANTES all 40's triple mutant and mlFN-β to the appropriate concentration.

Administration Route

Triple 40's RANTES mutant, Triple 40's Met-RANTES mutant and m-IFN-β were administered daily by i.p. route at the volume of administration of 200 μl/mouse. Groups 1, 2 were dosed i.p. with 200 μl/mouse of PBS.

Duration of Treatment

The treatment started for each animal at experimental day 4 (approximately 3-5 days before the usual occurrence of the disease) and then continued for 14 consecutive days (sacrifice of animals at experimental day 18)

Clinical Observations

Starting from day 5 the animals were individually examined for the presence of paralysis by means of a clinical score as follows:

0=no sign of disease 0.5=partial tail paralysis

1=tail paralysis 1.5=tail paralysis+partial unilateral hindlimb paralysis

2=tail paralysis+hindlimb weakness or partial hindlimb paralysis 2.5=tail paralysis+partial hindlimb paralysis (lowered pelvi)

3=tail paralysis+complete hindlimb paralysis 3.5=tail paralysis+complete hindlimb paralysis+incontinence 4=tail paralysis+hindlimb paralysis+weakness or partial paralysis of forelimbs 5=moribund or dead 2. Results a) Heparin Binding Assays The purified RANTES proteins mutated in one or in three positions were analysed by heparin chromatography and the concentration of NaCl required to elute them was compared to the elution profile of WT RANTES. Since the interaction with heparin is electrostatic, the mutants were also subjected to cation exchange chromatography on a MonoS column. This results in a drop in NaCl concentration required to elute them since the mutagenesis has removed basic residues. The difference in NaCl concentration obtained on cation exchange chromatography is subtracted from that obtained on Heparin chromatography. If this value is positive, a specific interaction with heparin is identified. (Table 1).

Figure 3:
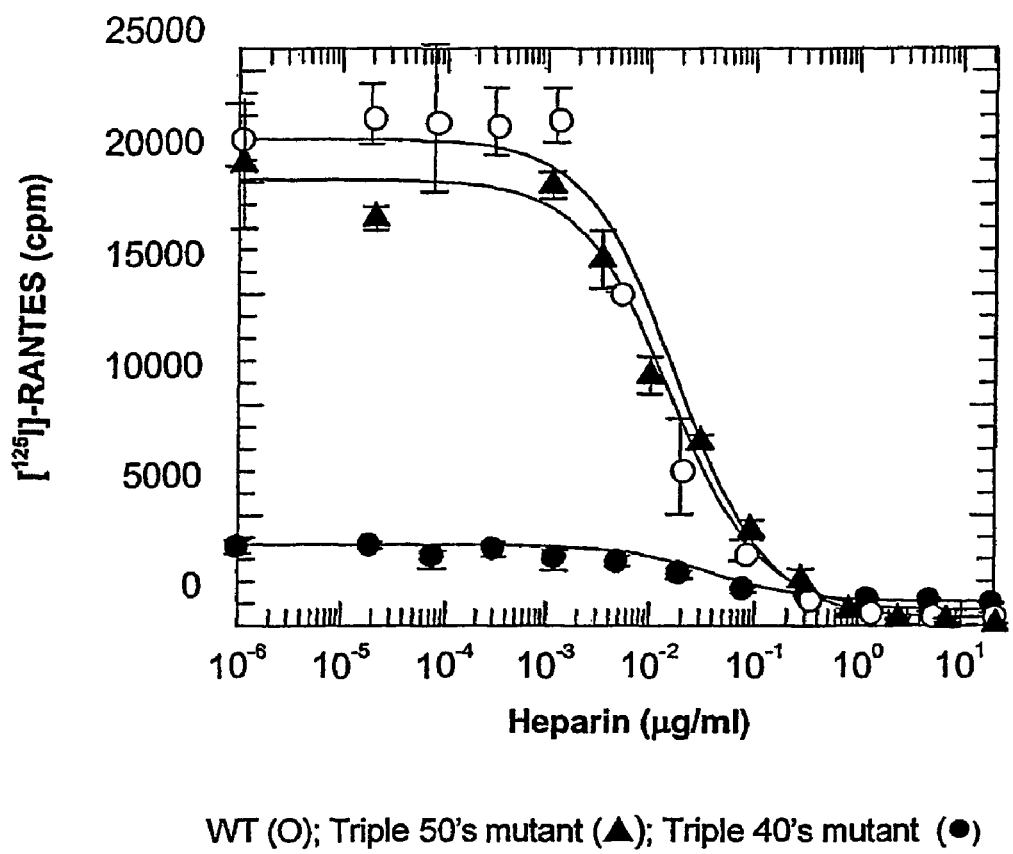
FIG. 3: it shows the results of the Competition Binding Assay of [$^{125}$I]-RANTES and mutants by heparin in the heparin bead assay.

A direct measure of binding to heparin was performed with the triple 40's and 50's RANTES mutants in a competition binding assay. The WT RANTES and the mutants were iodinated by Amersham and all had the same specific radioactivity of 2,200 mCi/mole. However, only approximately 20% of the triple 40's mutant bound to the heparin beads, with a maximum number of cpm of 4,000 compared to 22,000 cpm for wr RANTES and the 50's mutant (FIG. 3). This demonstrates that these residues in the 40's loop, which have been mutated, contribute to the majority of the heparin binding capacity of RANTES. On the other side, this also demonstrates that the putative GAG-binding motif in the 50's loop is not a "true" GAG-binding site.

b) Equilibrium Competition Receptor Binding Assays

Figure 4:
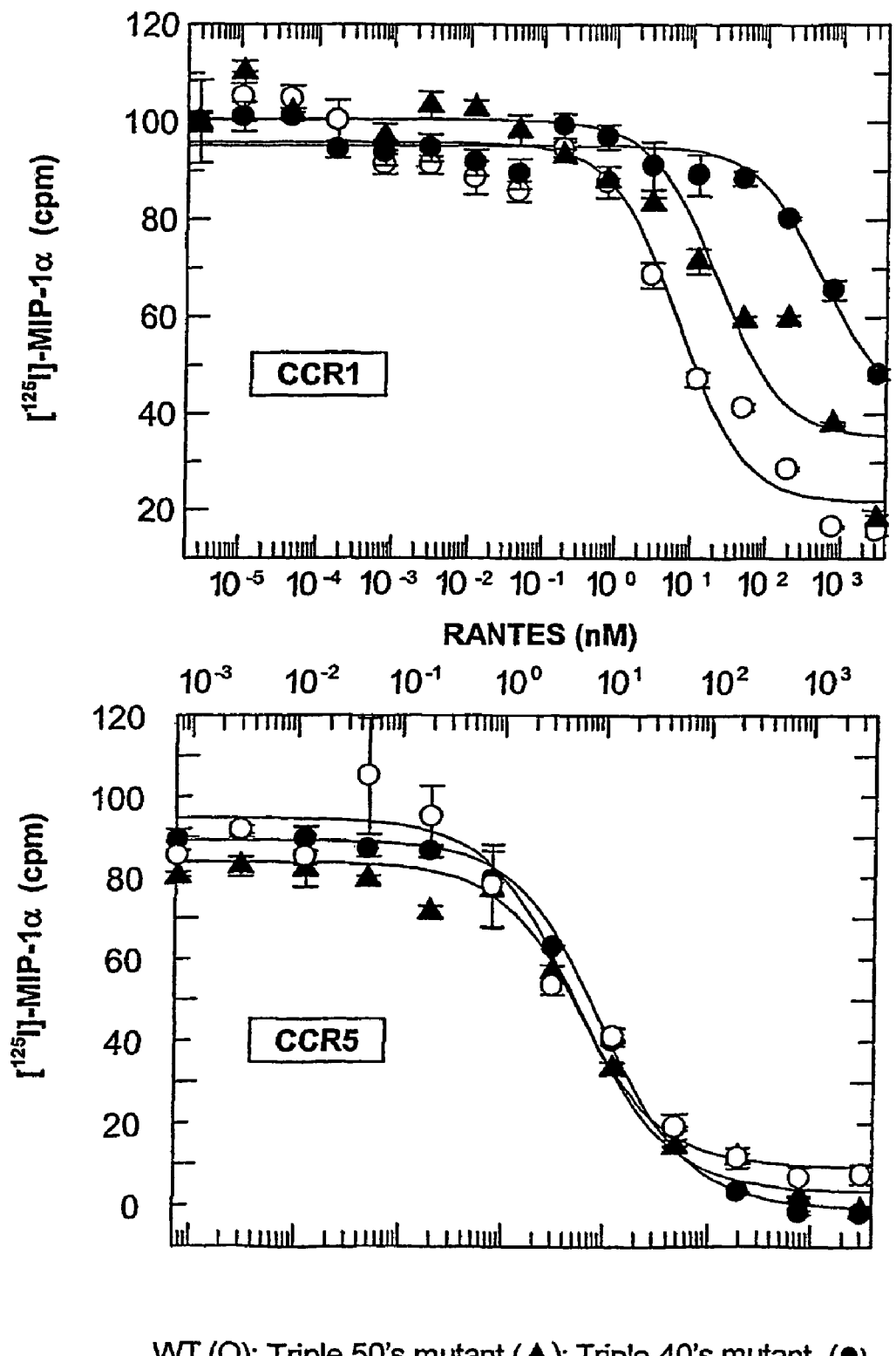
FIG. 4: it reports the Competition Equilibrium Binding Assays of RANTES and the triple 40's RANTES mutant.

The ability of the triple 40's and triple 50's RANTES mutants to compete for [$^{125}$I] MIP-1α for binding to recombinant CCR1 and CCR5 in membranes prepared from CHO stable transfectants. There was no significant difference in any of the single mutations on both receptors (results not shown). Neither of the triple mutants showed a difference in binding to CCR5 compared to the WT RANTES protein. However, on CCR1, the triple 40's mutant had a 100-fold reduction in affinity, whereas the triple 50's mutant only showed a small (3-fold) loss of affinity (FIG. 4).

c) Chemotaxis Assays

Figure 5:
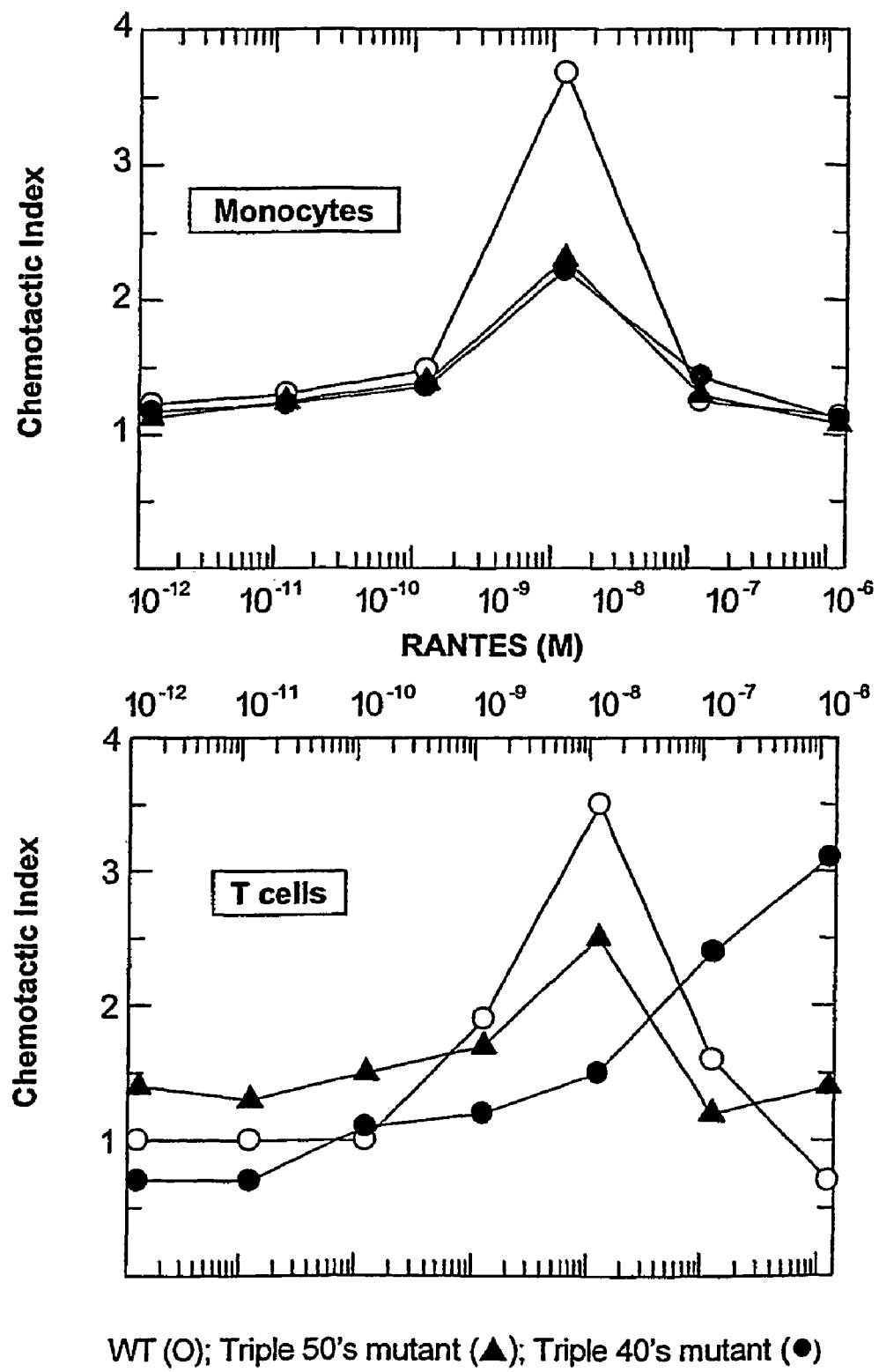
FIG. 5: it shows the induction of monocyte and of T cell chemotaxis by RANTES and the triple 40's and 50's RANTES mutants.

The triple 40's and triple 50's mutants were all able to induce monocyte chemotaxis with activities comparable to WT RANTES, with the exception of the triple 40's mutant which was only able to induce significant chemotaxis at 1 μM. However the triple 40's and 50's mutants were equipotent in their ability to induce T cell chemotaxis (FIG. 5). The results obtained in the monocyte chemotaxis assays correspond well with those obtained in the receptor binding assays.

The results obtained in the monocyte chemotaxis assays correspond well with those obtained in the receptor binding assays. The loss of activity of the triple 40's RANTES mutant on monocyte chemotaxis corresponds to the loss of affinity for CCR1.

d) Peritoneal Cellular Recruitment Assays

Figure 6:
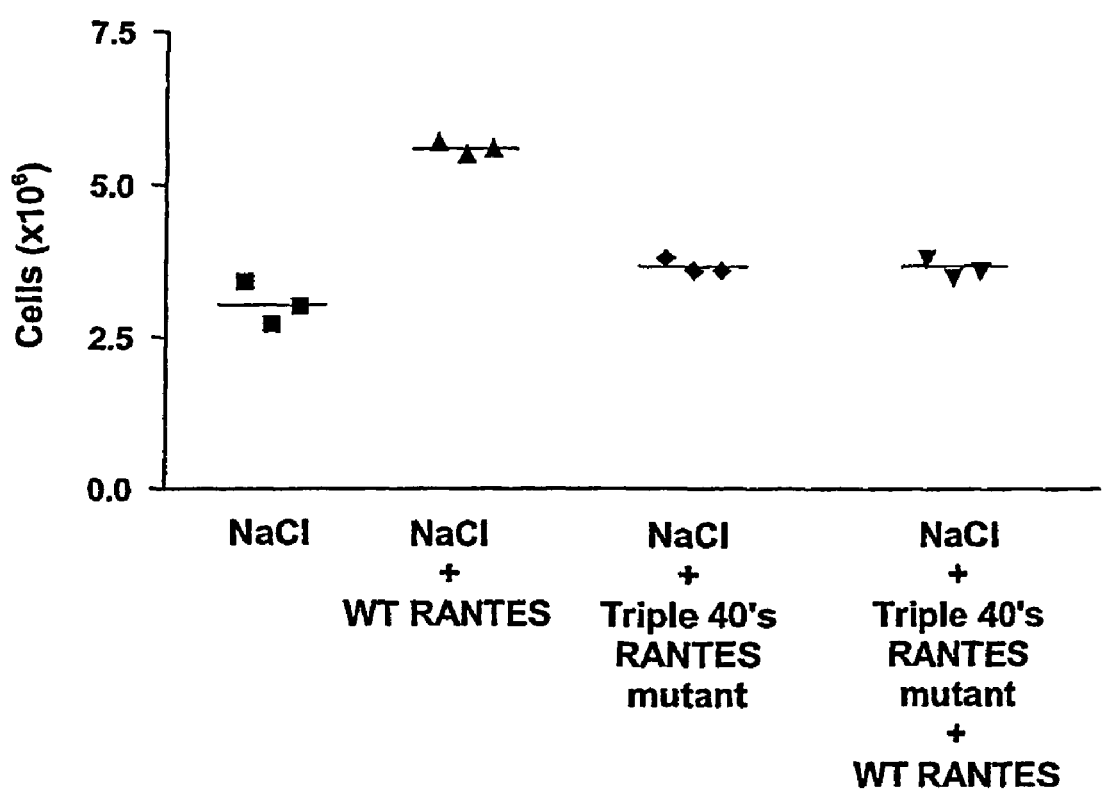
FIG. 6: it shows the inhibition of peritoneal cell recruitment by the triple 40's RANTES mutant.

The triple 40's RANTES mutant was not able to induce cellular recruitment into the peritoneum at the dose (10 μg/mouse) that RANTES causes substantial recruitment (FIG. 6).

Furthermore, if 10 μg of the mutant is administered 30 minutes prior to the administration of RANTES, the cellular recruitment induced by RANTES is inhibited. Therefore abrogation of GAG-binding produced an inhibitor of chemokine-induced cellular recruitment in vivo.

Figure 7:
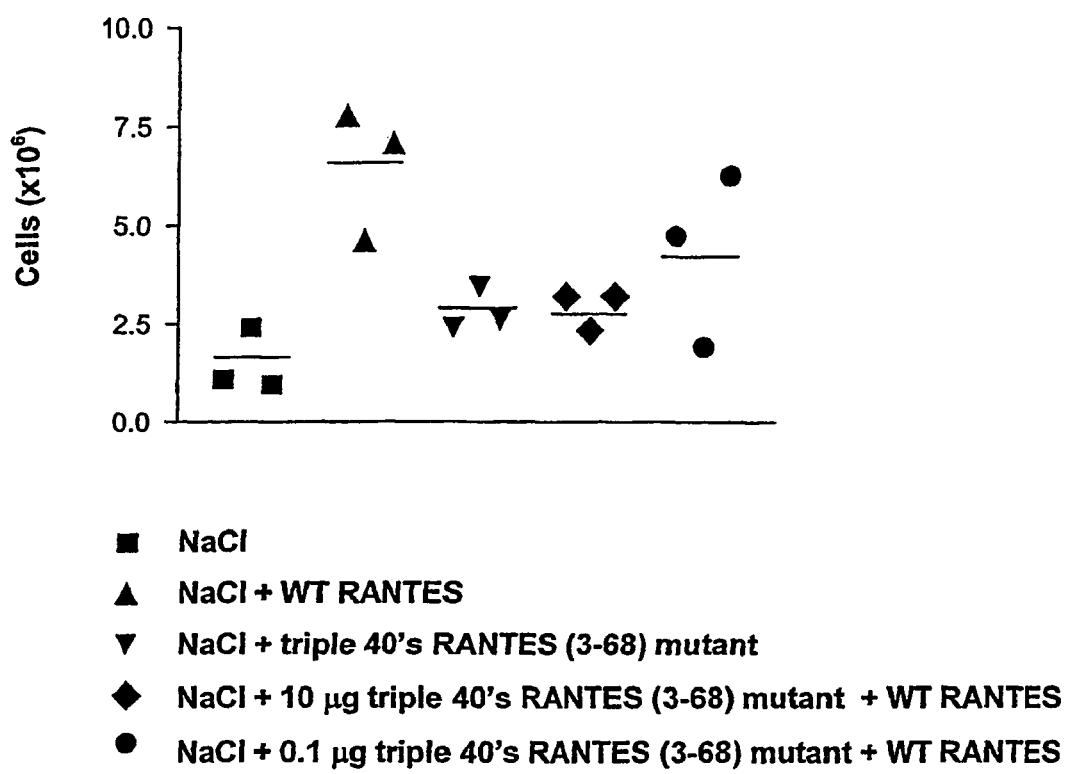
FIG. 7: it shows the inhibition of RANTES induced peritoneal cellular recruitment by truncated triple 40's RANTES (3-68) mutant produced in *Pichia pastoris*.
Figure 8:
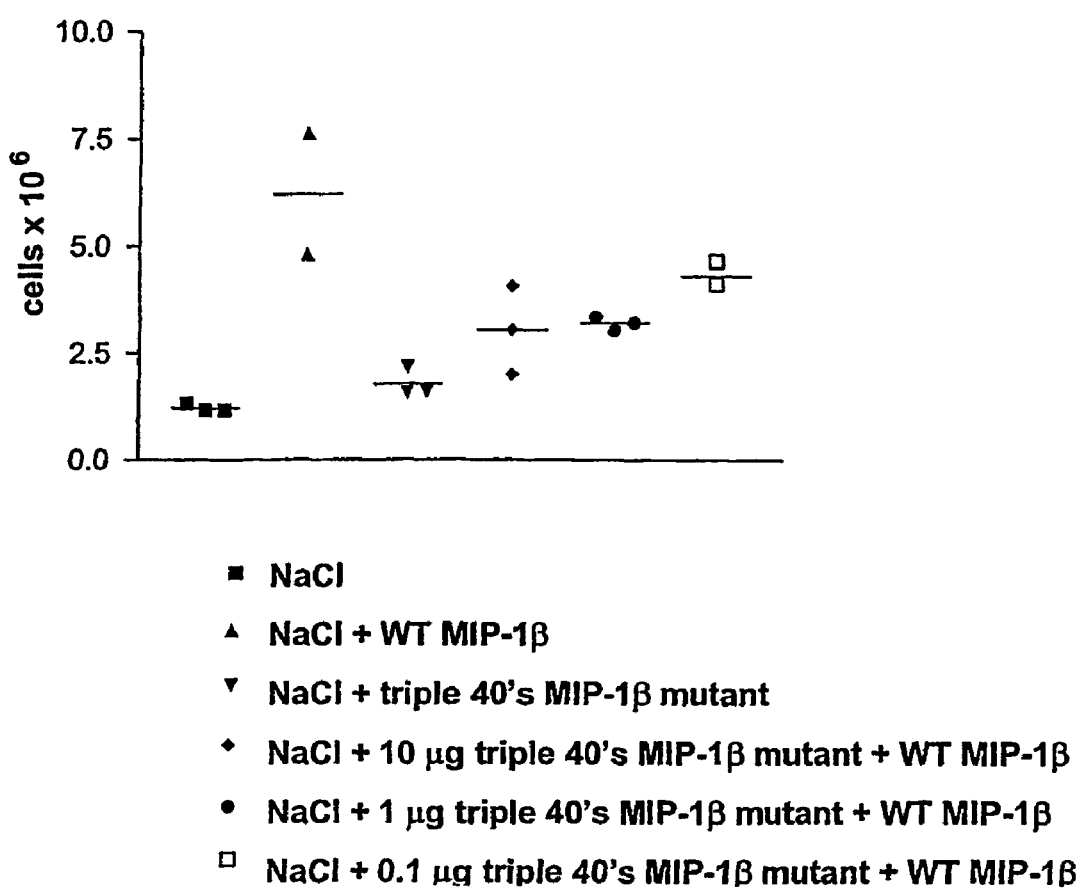
FIG. 8: it shows the inhibition of MIP-1β induced pertoneal cellular recruitment by the MIP-1β triple 40's mutant (K45AR46AK48A).
Figure 9:
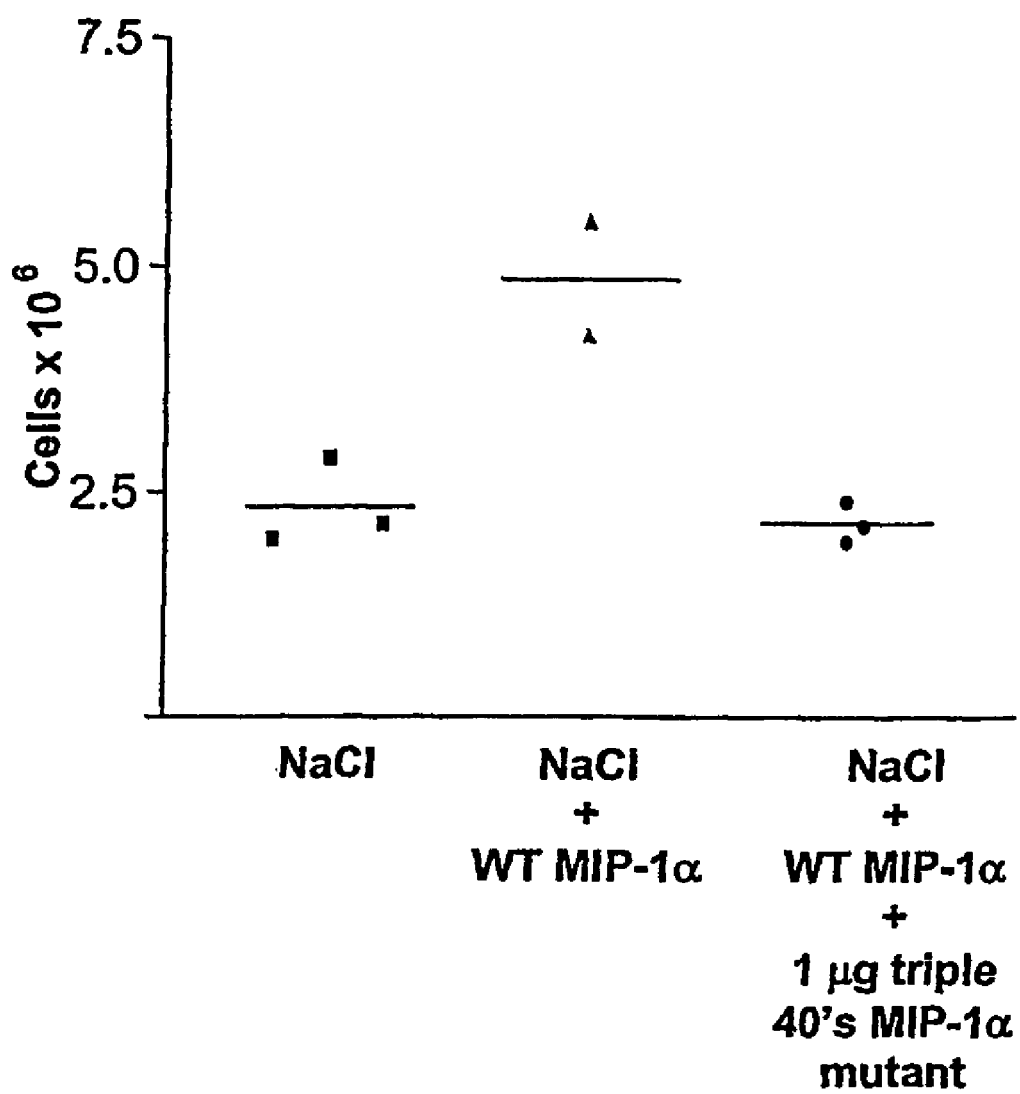
FIG. 9: it shows the inhibition of MIP-1α induced peritoneal cellular recruitment by the triple MIP-1α mutant (R18A-R46A-R48A).

Analogous results are shown in FIG. 7 with truncated RANTES (3-68) triple 40's mutant (produced in *Pichia pastoris*), in FIG. 8 by MIP-1β triple 40's mutant (K45A-R46A-K48A, and in FIG. 9 by MIP-1α triple 40's mutant (R18A-R46A-R48A). The cellular recruitment stimulated by thioglycollate was inhibited as well by the triple 40's RANTES mutant, as it shown in FIG. 10.

e) Experimental Autoimmune Encephalomyelitis (EAE)

Figure 11:
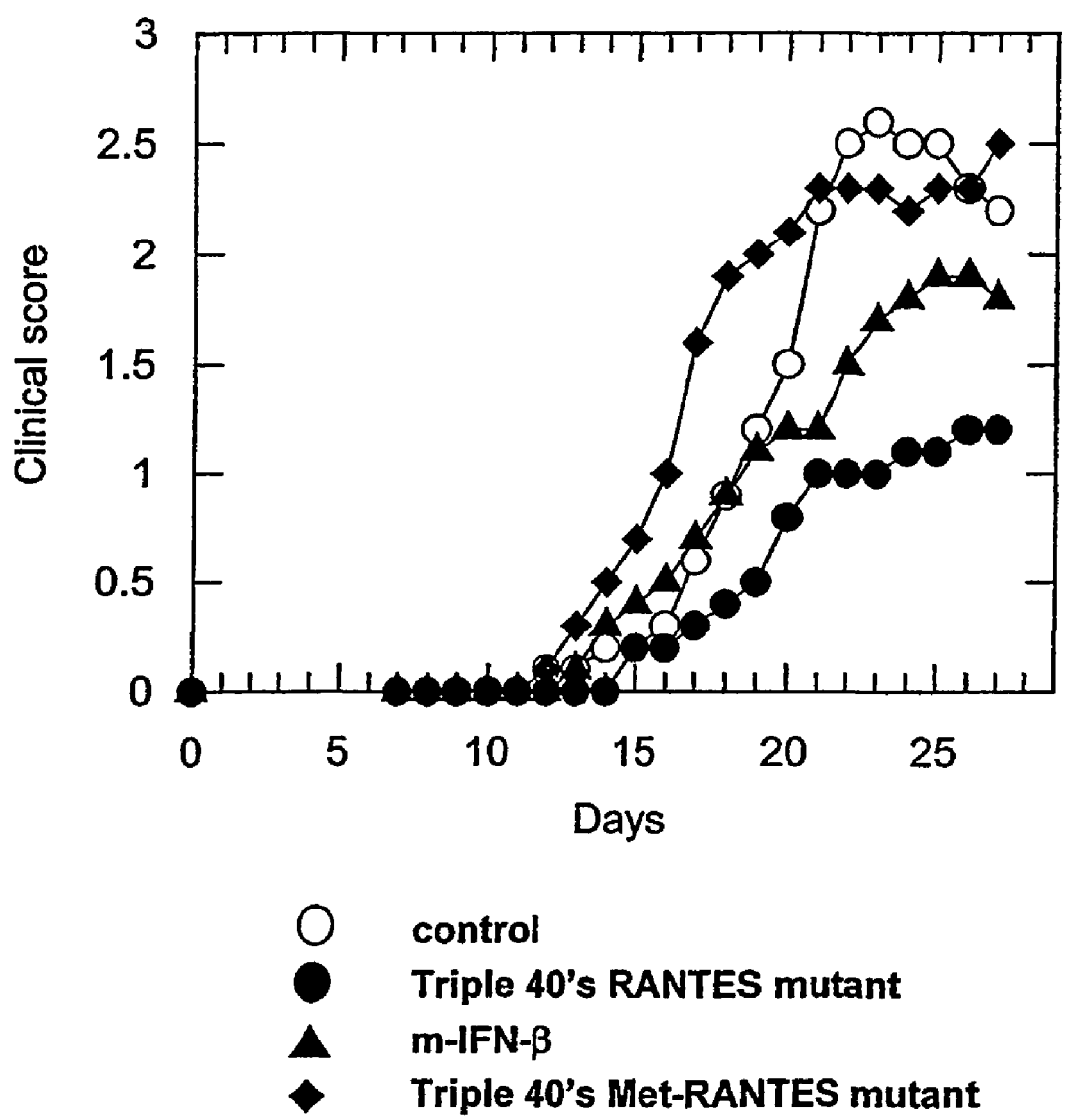
FIG. 11: it shows the inhibition of the onset of Experimental Autoimmune Encephalomielitis by the all-40's RANTES triple mutant of the invention.

The triple 40's RANTES mutant showed a dose-related effect in the murine EAE model. The protein, at both 1 μg and 10 μg/mouse administered daily i.p starting on day 10 post the primary immunization with MOG, demonstrated a comparable efficacy to the reference treatment, recombinant M-IFN-β (FIG. 11). The onset of disease was significantly delayed and the disease severity (as assessed by the area under the curve) was also significantly reduced. Furthermore, the mean of the maximum clinical score reached during the experiment was also decreased. The other mutant (triple 40's Met-RANTES mutant) failed to show any beneficial effect in the same experiment.

Our results show a clear beneficial effect of the treatment with the all-40's RANTES triple mutant, which reduces clinical signs of chronic EAE in mice after immunization with MOG. Therefore, the triple 40's RANTES mutant has a beneficial therapeutic effect, and can be used as treatment, in chronic demyelinating diseases such as MS.

TABLE 1

Molarity NaCl to elute from Heparin and Mono-S (cation exchange) columns

| RANTES Mutation | Heparin | MonoS | Δ NaCl$^{Hep-S}$ | Δ NaCl$^{Mono-s}$ | ΔΔ NaCl |
|---|---|---|---|---|---|
| No (WT) | 0.80 | 0.91 | — | — | — |
| R44A | 0.61 | 0.82 | 0.19 | 0.09 | 0.10 |
| K45A | 0.65 | 0.97 | 0.15 | 0.04 | 0.11 |
| R47A | 0.65 | 0.84 | 0.15 | 0.07 | 0.08 |
| R44A-K45A-R47A | 0.47 | 0.70 | 0.33 | 0.21 | 0.11 |
| K55A | 0.70 | 0.86 | 0.10 | 0.05 | −0.05 |
| K56A | 0.90 | 0.94 | −0.10 | 0.07 | −0.17 |
| R59A | 0.79 | 0.85 | 0.01 | 0.06 | −0.05 |
| K55A-K56A-R59A | 0.70 | 0.75 | 0.10 | 0.16 | −0.06 |

The following Table 2 will clarify the identity of the sequences reported in the Sequence Listing and throughout the text.

TABLE 2

| SEQ ID NO: | Sequence description |
|---|---|
| 1 | WILD TYPE (WT) RANTES |
| 3 | TRIPLE 40'S RANTES MUTANT |
| 2 | TRIPLE 40'S RANTES (3-68) MUTANT |
| 4 | TRIPLE MIP-1-alpha MUTANT (R18A-R46A-R48A) |
| 5 | TRIPLE MIP-1-beta MUTANT (K45A-R46A-K48A) |
| 6 | TRIPLE 50'S RANTES MUTANT |
| 7 | TRIPLE 40'S Met-RANTES MUTANT |
| 8 | R44A-RANTES MUTANT |
| 9 | K45A-RANTES MUTANT |
| 10 | R47A-RANTES MUTANT |
| 11 | K55A-RANTES MUTANT |
| 12 | K56A-RANTES MUTANT |
| 13 | R59A-RANTES MUTANT |
| 14 | Primer P1 |
| 15 | Primer P2 |
| 16 | Primer P3 |
| 17 | Primer P4 |
| 18 | Primer P5 |
| 19 | Primer P6 |
| 20 | Primer P7 |
| 21 | Primer P8 |
| 22 | Primer P9 |
| 23 | Primer P10 |
| 24 | Primer P11 |
| 25 | Primer P112 |
| 26 | Primer P13 |
| 27 | Primer P14 |
| 28 | Primer P15 |
| 29 | Primer P16 |
| 30 | WT-I309 |
| 31 | WT-MIP-1-alpha |
| 32 | WT-MIP-5 |
| 33 | WT-MIP-4 |
| 34 | WT-MIP-3 |
| 35 | WT-HCC1 |
| 36 | WT-I36512 |
| 37 | WT-MCP-2 |
| 38 | WT-MIP-1-beta |

The invention claimed is:

1. A mutated human RANTES, consisting of the amino acid sequence of SEQ ID NO:2.

2. A pharmaceutical composition for the treatment of multiple sclerosis, comprising as an active ingredient the mutant human RANTES of claim 1 together with a pharmaceutically acceptable excipient.

* * * * *